United States Patent [19]

Lin

[11] 4,069,263
[45] Jan. 17, 1978

[54] PROCESS FOR DIRECTED CHLORINATION OF ALKYLBENZENES

[75] Inventor: Henry C. Lin, Grand Island, N.Y.

[73] Assignee: Hooker Chemicals & Plastics Corporation, Niagara Falls, N.Y.

[21] Appl. No.: 756,449

[22] Filed: Jan. 3, 1977

[51] Int. Cl.$^2$ .............................................. C07C 25/04
[52] U.S. Cl. .......................... 260/650 R; 252/429 R
[58] Field of Search ..................................... 260/650 R

[56] References Cited

U.S. PATENT DOCUMENTS

| 1,741,305 | 12/1929 | Jaeger | 260/650 R |
|---|---|---|---|
| 1,946,040 | 2/1934 | Stoesser et al. | 260/650 R |
| 3,226,447 | 12/1965 | Bing et al. | 260/650 R |
| 4,013,142 | 6/1977 | Graham | 260/650 R |
| 4,013,147 | 6/1977 | Graham | 260/650 R |

*Primary Examiner*—C. Davis
*Attorney, Agent, or Firm*—Peter F. Casella; William J. Cossetta, Jr.; Arthur S. Cookfair

[57] ABSTRACT

A process for the production of nuclear chlorinated alkylbenzenes comprises reacting, in the liquid phase, alkylbenzene with chlorine in the presence of a Lewis acid catalyst and a co-catalyst comprising a thianthrene compound or mixture of thianthrene compounds characterized by the formula:

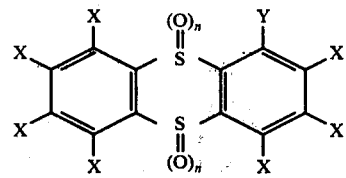

where $n$ is 0 to 1, $y$ is an electron-withdrawing substituent or an electron-donating substituent and each $x$ is hydrogen, an electron-withdrawing substituent or an electron-donating substituent with the proviso that the total number of electron-withdrawing substituents present at the $x$ and $y$ positions is at least one and no more than seven; the total number of electron-donating substituents is at least one and no more than four; no more than three electron-donating substituents are present at the peripositions; and when electron-withdrawing substituents are present at each of the peri-positions, electron-donating substituents are present at each of the 2, 3, 7 and 8 positions.

20 Claims, No Drawings

PROCESS FOR DIRECTED CHLORINATION OF ALKYLBENZENES

BACKGROUND OF THE INVENTION

The chemical reaction of chlorine with alkylbenzenes, such as toluene, to prepare nuclear substitued chloro-compounds such as monochlorotoluene, is well known and of considerable commercial importance. Such reactions are generally carried out in the presence of a chlorination catalyst such as antimony chloride, ferric chloride, aluminum chloride, and the like. The usual products of such reactions are a mixture of various mono-chlorinated and/or polychlorinated compounds and various positional isomers of these. For example, in the liquid phase substitution-chlorination of toluene, by reaction of chlorine and toluene, to form monochlorotoluene, the usual product is a mixture of orthochlorotoluene and parachlorotoluene which may, in addition, contain varying amounts of other chlorinated products such as metachlorotoluene, dichlorotoluene, polychlorotoluenes and benzylic chlorides. Of the major reaction products, that is orthochlorotoluene and parachlorotoluene, the latter is the most commercially valuable. In the past, considerable effort has been expended in attempts to direct the chlorination reaction in such a manner as to lower the ratio of orthochlorotoluene to parachlorotoluene, that is, to discover reaction conditions under which the formation of parachlorotoluene is favored. Thus, for example, it is known from U.S. Pat. No. 1,946,040 that when alkylbenzenes are reacted with chlorine, the yield of parachlorinated product is improved with the aid of a mixed catalyst comprising sulfur and antimony trichloride and, optionally, iron or lead. In British Patent 1,153,746 (1969) it is disclosed that in the chlorination of toluene in the presence of a ring chlorination catalyst, such as ferric chloride, antimony chloride, and the like, the ratio of orthochloro to parachloro isomers produced may be lowered by the presence of an organic sulfur compound such as thiophene, hexadecylmercaptan, dibenzothiophene or the like. Furthermore, in British Patent 1,163,927 (1969) it is disclosed that the proportion of parachlorotoluene produced may be improved when toluene is chlorinated in the presence of elemental sulfur or an inorganic sulfur compound and a ring-chlorination catalyst such as ferric chloride, aluminum chloride, antimony chloride, zinc chloride, iodine, molybdenum chloride, stannous chloride, zirconium tetrachloride or boron trifluoride. In U.S. Pat. No. 3,226,447, issued December 28, 1965 to Bing et al, it is disclosed that in the substitution-chlorination of benzene and toluene, the ratio of ortho isomer to para isomer in the chlorinated product may be lowered when the reaction is carried out in the presence of an iron, aluminum or antimony halide catalyst and a co-catalyst which is an organic sulfur compound wherein the sulfur is divalent. Examples of such co-catalyst include various mercaptans, mercapto-aliphatic carboxylic acids, aliphatic thiocarboxylic acids, alkyl sulfides, alkyl disulfides, thiophenols, aryl sulfides, aryl disulfides and the like containing divalent sulfur. The use of such co-catalysts in the chlorination of toluene produces a product wherein the ratio of orthochlorotoluene to parachlorotoluene is 1.2, indicating a considerable improvement over the ortho to para isomer ratio achieved in the absence of the co-catalyst. However, it will be apparent that even a 1.2, ratio of ortho to para isomer represents a considerable economic disadvantage in the production of substantial amounts — greater than 50 percent of the monochlorotoluene mixture — of the unwanted ortho isomer. Thus, it will be apparent that a considerable commercial benefit is to be derived from a still further lowering of the ortho to para isomer ratio.

Still further improvements in the preparation of monochlorotoluene having a low ortho to para isomer ratio are disclosed in co-pending applications Ser. Nos. 601,219 and 601,690 to John C. Graham, now U.S. Pat. Nos. 4,031,147 and 4,031,142, respectively. Co-pending application Ser. No. 601,690 discloses a process for the preparation of nuclear chlorinated alkylbenzenes, such as monochlorotoluene which comprises reacting an alkylbenzene, such as toluene, with chlorine in the presence of a Lewis acid catalyst and, as a co-catalyst, thianthrene. When toluene is chlorinated in accordance with the process disclosed in co-pending application Ser. No. 601, 690, a monochlorotoluene product having an ortho to para isomer ratio of about 1.0 is obtainable.

In accordance with co-pending application Ser. No. 601,219, a monochlorotoluene product having an ortho to para isomer ratio of less than about 1.0 is obtainable with the aid of a co-catalyst comprising a thianthrene compound having electron-withdrawing substituents, such as chlorine, present on the nucleus thereof. Thus, in accordance with co-pending application Ser. No. 601,219, an alkylbenzene is reacted with chlorine in the presence of a Lewis acid catalyst and a co-catalyst comprising a thianthrene compound, or mixture of thianthrene compounds, characterized by the formula:

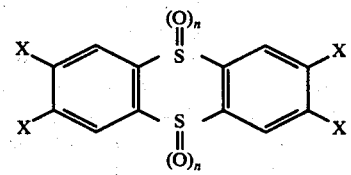

where each $n$ is 0 to 1, and each $x$ is hydrogen or an electron-withdrawing substituent.

Although the processes of co-pending application Ser. Nos. 601,219 and 601,690 provide superior results to the prior art discussed above it will be apparent that still further improvements would be desirable and of commercial benefit. Furthermore, the co-catalyst, especially the chlorinated thianthrene cocatalyst of Ser. No. 601,219 is synthesized by a two-step reaction from a specific and limited selection of raw materials. Thus, it will be seen that an advantage is to be derived from the use of a co-catalyst that may be more easily synthesized from readily available raw materials.

It is an object of the present invention to provide an improved process for the directed nuclear chlorination of aromatic compounds. It is a further object to provide a process for the directed nuclear chlorination of alkylbenzens, especially toluene, whereby the chlorinated product is characterized by a desirably low ratio of orthochloro to parachloro isomers. It is a still further object to provide an improved para-directing co-catalyst for such processes, that may be conveniently synthesized from readily available raw materials. It is a still further object to provide a novel catalyst system based on a para-directing co-catalyst comprising a thianthrene compound or mixture of thianthrene compounds, having both electron-withdrawing substituents and electron-donating substituents on the nucleus thereof.

The thianthrene compounds employed as para-directing co-catalysts in accordance with this invention are described hereinbelow in accordance with the current Chemical Abstracts system whereby the numbering of ring positions is as follows:

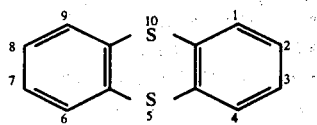

SUMMARY OF THE INVENTION

In accordance with the present invention there is provided a process for the production of nuclear chlorinated alkylbenzenes which comprises reacting, an alkylbenzene with chlorine in the presence of a catalyst system comprising a Lewis acid catalyst and a co-catalyst comprising a thianthrene compound or mixture of thianthrene compounds characterized by the formula:

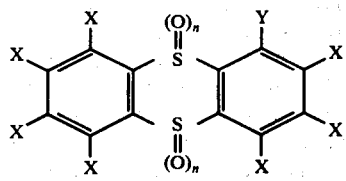

where $n$ is 0 to 1, $y$ is an electron-withdrawing substituent or an electron-donating substiuent and each $x$ is hydrogen, an electron-withdrawing substituent or an electron-donating substituent with the proviso that the total number of electron-withdrwing substituents present at the $x$ and $y$ positions is at least one and no more than seven; the total number of electron-donating substituents is at least one and no more than four; no more than three electron-donating substituents are present at the peripositions; and when electron-withdrawing substituents are present at each of the peri-positions, electron-donating substituents are present at each of the 2, 3, 7 and 8 positions.

The co-catalysts suitable for use in the process of this invention are characterized by the formula shown hereinabove and include, for example, thianthrene compounds, as well as the analgous mono- or di-sulfoxide compounds, wherein one or more electron-withdrawing substitents and one or more electron-donating substituents are present in the positions designated, as well as mixtures of such compounds. When more than one electron-donating substituent is present on the thianthrene nucleus, the substituents may be the same or different. Suitable electron-donating substituents include, for example, alkyl and alkoxy groups. Preferably the electron-donating substituents are lower alkyl or alkoxy of 1 to 12 carbon atoms, and most preferably, methyl. When more than one electron-withdrawing substituent is present on the thianthrene nucleus, the substituents may be the same or different. Suitable electron-withdrawing substituents which may be present on the thianthrene or thianthrene oxide nucleus include for example, halo-, alkanoyl-, nitro-, sulfonyl-, cyano-, quarternary amino-, trifluoromethyl groups and the like, the preferred electron-withdrawing substituents being chloro-, fluoro-, bromo-, acetyl-, benzoyl, and trifluoromethyl and most preferably, chloro-.

The para-directing co-catalysts of the present invention differ substantially from the thianthrene co-catalysts of the prior art in that at least one electron-donating substituent is present on the thianthrene nucleus and further, that an electron-donating substituent or an electron-withdrawing substituent is present at one or more of the peri-positions. Prior to the present invention it was considered that the presence of an electron-donating substituent on the thianthrene nucleus would be disadvantageous and would most likely diminish or negate the para-directing catalytic effect. Methylthianthrenes, such as 2,3,7,8-tetramethylthianthrene have been found to be substantially ineffective as para-directing co-catalysts when employed with a Lewis acid catalyst in the chlorination of toluene, giving ortho;para isomer ratios in the range of about 1.1 to 1.5. Furthermore, prior to the present invention, it was considered that the presence of a substituent other than hydrogen at the peri-position of the thianthrene nucleus, that is, positions 1,4,6 and 9, adjacent to the sulfur atoms, would inhibit or lessen the para-directing effect of the thianthrene compound. It is surprising therefore, in accordance with this invention, to find that the para-directing catalytic activity of a thianthrene compound may actually be enhanced by the presence of one or more electron-donating substituents, such as methyl substituents, and the presence of either an electron-withdrawing substituent or an electron-donating substituent at one or more of the peri-positions of judiciously selected thianthrene compounds.

The preferred co-catalysts of this invention are the thianthrene compounds and mixtures thereof characterized by the formula shown hereinabove where $n$ is 0, and two to four methyl groups and four to six chlorine atoms are present on the thianthrene nucleus in the positions designated. Most preferred are the dimethylhexachlorothianthrenes, dimethylpentachlorothianthrenes and dimethyltetrachlorothianthrenes and mixtures thereof.

The thianthrene compounds employed as co-catalyst in accordance with this invention may be prepared by reacting an appropriately substituted benzene compound with sulfur monochloride in the presence of aluminum chloride. The resultant substituted thianthrene compound may be further substituted, as desired, for example by chlorination. The substituted benzene starting compound may be selected on the basis of the substituents desired in the final thianthrene product. Thus for example, an excess of orthochlorortoluene may be reacted with sulfur monochloride (as the limiting reactant) in the presence of aluminum chloride (typically in a molar ratio of $AlCl_3:S_2Cl_2$ of about 0.8:1.0) at a temperature of about 50° Celsius to produce dimethyldichlorothianthrene as a mixture of 2,7-dimethyl-3,8-dichloro-, and 2,8-dimethyl-3,7-dichloro-isomers. The product may then be further reacted for example with chlorine in situ or in a solvent such as nitrobenzene to produce such derivatives as dimethyltetrachlorothianthrene, dimethylpentachlorothianthrene and dimethylhexachlorothianthrene. In a similar manner, various other appropriately substituted benzene compounds may be employed as starting materials to prepare other substituted thianthrene compounds useful as co-catalysts in the process of this invention. In some instances the thianthene compounds prepared are mixtures predominantly composed of thianthrene compounds or isomers characterized by the formula shown hereinabove. Such mixtures may be separated and the pure compounds employed as co-catalysts in accordance with this invention. However, in instances where the thianthrene compounds are prepared as mixtures, it has been found convenient and effective to employ the mixture as a co-catalyst without the need for separation into individual components.

A wide variety of known Lewis acid catalysts may be employed in the process of the present invention. The term "Lewis acid catalyst" as employed herein includes, in addition to Lewis acids, those compounds or elements that will form or function as Lewis acids under the conditions of the chlorination reaction. Preferred catalysts for this purpose are compounds of antimony, lead, iron, molybdenum and aluminum, including for example, the halides, oxyhalides, oxides, sulfides, sulfates, carbonyls and elemental form of these elements and mixtures of such compounds and most preferably the chlorides, oxychlorides, oxides and elemental forms of antimony and iron. Typical of the catalysts which may be employed in the process of this invention are aluminum chloride, antimony thrichloride, antimony pentachloride, antimony trioxide, antimony tetraoxide, antimony pentaoxide, antimony trifluoride, antimony oxychloride, molybdenum hexacarbonyl, lead sulfide, ferric chloride, ferrous chloride, ferrous sulfate, ferric oxide, ferrous sulfide, iron disulfide, iron pentacarbonyl, iron metal, and the like.

The amounts of catalyst and co-catalyst employed may vary considerably. Substantial benefits in terms of the lowering of the ratio of ortho- to para- isomer in the product may be achieved, for example, when the catalyst and co-catalyst are present in a total amount ranging from less than about 0.01 percent to about 5 percent by weight or more, based on the weight of alkylbenzene, and preferably in a molar ratio of catalyst:co-catalyst of about 0.01:1 to about 10:1. However, based on effectiveness as well as economic considerations, it is preferred to employ the catalyst and co-catalyst in a total amount of about 0.01 to about 2.0 weight percent, based on the weight of alkylbenzene and in a molar ratio of catalyst:co-catalyst of less than about 4:1 and most preferably about 0.10:1 to about 1:1.

Under atmospheric pressure, the chlorination reaction of the present invention may be carried out over a wide range of temperatures, ranging for example from sub-zero temperatures such as $-30°$ Celsius or below to over 100° Celsius. The upper limit of temperature is, of course, determined by the boiling point of the reaction mixture, and may, depending on the boiling point limitation, range as high as 150° Celsius or higher. However, no practical advantage is gained through the use of higher temperatures or extremely low temperatures, and it is preferred to utilize temperatures in the range of about $-20°$ to about 110° Celsius, and most preferably in the range of about 0° to about 70° Celsius. The optimum temperature will vary somewhat, depending on the particular catalyst system employed.

Although it is preferred to carry out the process at atmospheric pressures, subatmospheric or superatmospheric pressures may be employed if desired.

The alkylbenzenes which may be chlorinated in accordance with the present invention include the various straight chain and branched chain alkylbenzenes as well as substituted alkylbenzenes. The preferred alkyl benzenes are those wherein the alkyl group is 1 to 4 carbon atoms, and most preferably toluene. In the chlorination of toluene in accordance with this invention, monochlorotoluene products having a ratio of orthochlorotoluene/parachlorotoluene of less than about 1.0 are obtainable. It will be appreciated that, although the preparation of monochloro alkylbenzenes, having a relatively high proportion of parachloro alkylbenzene, is an important object of the present invention, the monochloro product may be further chlorinated, if desired, to produce higher chlorinated derivatives.

The process of this invention may be carried out by chlorination of the alkylbenzene in solution or in the absence of a solvent. Suitable solvents which may be employed, if desired, include for example various halogenated solvents such as carbon tetrachloride, or aromatic solvents such as monochlorobenzene. It is preferred, however, to carry out the chlorination directly, in the absence of a solvent.

The following specific examples are provided to further illustrate this invention and the manner in which it may be carried out. It will be understood, however, that the specific details given in the examples have been chosen for purpose of illustration and are not to be construed as a limitation of the invention. In the examples, unless otherwise indicated, all parts and percentages are by weight and all temperatures are in degrees Celsius. Product analyses were obtained using gas chromatographic techniques.

The following Examples 1a, 1b and 1c illustrate methods of preparation of the thianthrene compounds useful as co-catalysts in accordance with this invention.

EXAMPLE 1a

A mixture of 635.2 parts of o-chlorotoluene and 100 parts of aluminum trichloride was placed on an icewater bath and stirred while 120 parts of sulfur monochloride was added dropwise. After completion of the addition, the reaction mixture was heated on a water bath for 3 hours, then cooled to room temperature. The reaction mixture was filtered and the solid collected was washed several times with orthochlorotoluene and dried. Analysis of the product by gas chromatographic techniques indicated the composition to be 4.4 percent dimethylthianthrene; 51.4 percent dimethylchlorothianthrene; and 44.2 percent dimethyldichlorothianthrene.

A mixture of 50 parts of this product with 470 parts of nitromethane solvent, was stirred and maintained at about 50° C, while a stream of chlorine gas (43 parts) was slowly passed into the mixture. At the end of the chlorine addition a yellow solid precipitated and was collected by filtration, washed with acetone and ethanol, and dried to yield 50 parts of a mixture of 8.93% dimethyltrichlorothianthrene; 5.03% dimethyltetrachlorothianthrene; 64.61 % dimethylpentachlorothianthrene; and 21.53 % dimethylhexachlorothianthrene.

EXAMPLE 1b

The procedure of Example 1a was repeated except that 2-nitropropane was substituted for the nitromethane solvent in the chlorination step and additional chlorine reactant (totalling 65 parts) was employed. Gas chromatographic analysis of the product indicated a composition of 10.56% dimethylpentachlorothianthrene and 89.44% dimethylhexachlorothianthrene.

EXAMPLE 1c

In a similar manner to that of Example 1a, except that parachlorotoluene was substituted for orthochlorotoluene, a product was obtained that was a mixture of 1,6-dimethyl-2,3,4,7,8,9-hexachlorothianthrene and 1,9-dimethyl-2,3,4,6,7,8-hexachlorothianthrene.

EXAMPLE 2

A mixture of 170 parts of toluene, 0.34 parts of antimony pentachloride, and 1.0 part of the dimethylchlorothianthrene mixture prepared as in Example 1a cooled to 0° and stirred while a stream of chlorine (64 parts) was slowly passed into the mixture. The reaction mixture was quenched with water, extracted with ether, washed with aqueous sodium bicarbonate, and dried over anhydrous magnesium sulfate. Analysis of the reaction product indicated 44.22% toluene; 22.38% orthochlorotoluene; 33.33% parachlorotoluene; and no benzyl chloride; with an ortho:para isomer ratio of 0.67.

EXAMPLE 3

The procedure of Example 2 was repeated except that quantity of reactants was varied to provide a reaction mixture of 170 parts of toluene, 0.17 parts of antimony pentachloride, 0.5 parts of the dimethylchlorothianthrene mixture prepared as in Example 1a and 57 parts of chlorine. Analysis of the reaction product indicated the product to have a composition of 49.18% toluene; 20.34% orthochlorotoluene; 30.38% parachlorotoluene; 0.09% dichlorotoluene and 0.01% benzyl chloride. The ratio of orthochlorotoluene:parachlorotoluene was 0.67.

EXAMPLE 4

The procedure of Example 2 was repeated except that quantity of co-catalyst was varied to provide 0.2 part of the dimethylchlorothianthrene mixture and 0.01 parts of Fe was substituted for the 0.34 parts of antimony pentachloride. Analysis of the reaction product indicated the product to have a composition of 47.13% toluene; 22.29% orthochlorotoluene; 30.46% parachlorotoluene; 0.10% dichlorotoluene and 0.01% benzyl chloride. The ratio of orthochlorotoluene:parachlorotoluene was 0.73.

EXAMPLE 5

For purposes of comparison, the procedure of Example 4 was repeated except that in place of the dimethylchlorothianthrene mixture employed as co-catalyst therein, there was substituted 2,3,7,8-tetrachlorothianthrene. Analysis of the reaction product indicated a composition of 48.57% toluene, 22.71% orthochlorotoluene; 28.52% parachlorotoluene; 0.18% dichlorotoluene, and 0.02% benzyl chloride. The ratio of orthochlorotoluene:parachlorotoluene was 0.80.

From a comparison of the above Example 5 with Example 4 it will be seen that under the same conditions the co-catalyst of the present invention provides a significant improvement in para-directing effect over that of the prior art catalyst, tetrachlorothianthrene.

EXAMPLE 6

The procedure of Example 4 was repeated except that the reaction temperature was maintained at 30° C. Analysis of the product indicated a composition of 51.11% toluene; 22.12% orthochlorotoluene; 26.63% parachlorotoluene; 0.12% dichlorotoluene; and 0.02% benzyl chloride. The ratio of orthochlorotoluene:parachlorotoluene was 0.83.

EXAMPLE 7

For purposes of comparison, the procedure of Example 6 was repeated except that in place of the dimethylchlorothianthrene mixture co-catalyst there was substituted 2,3,7,8-tetrachlorothianthrene. Product analysis indicated a composition of 64.63% toluene; 16.33% orthochlorotoluene; 18.98% parachlorotoluene; 0.05% dichlorotoluene, 0.01% benzyl chloride; and a ratio of orthochlorotoluene:parachlorotoluene of 0.86.

EXAMPLE 8

The procedure of Example 2 was repeated except that in place of the dimethylchlorothianthrene mixture co-catalyst there was substituted an equal amount of a co-catalyst prepared in accordance with Example 1c. The composition of the reaction product was 37.57% toluene; 27.61% orthochlorotoluene; 37.43% parachlorotoluene; 0.01% benzyl chloride; and 0.08% dichlorotoluene. A ratio of ortho:para isomers of 0.79 was obtained.

EXAMPLE 9a

The procedure of Example 2 was repeated except in place of the co-catalyst employed therein, there was substituted 0.91 parts of 1,4,6,9-tetrachloro-2,3,7,8-tetramethylthianthrene co-catalyst. Analysis of the reaction product indicated a composition of 55.95% toluene; 19.38% orthochlorotoluene; 23.58% parachlorotoluene; 0.88% benzyl chloride and 0.21% dichlorotoluene. The ratio of ortho:para isomers obtained was 0.82.

EXAMPLE 9b

The procedure of Example 9a was repeated except that the reaction temperature was maintained at 30° C. Analysis of the resultant product indicated a composition of 39.79% toluene; 26.40% orthochlorotoluene; 33.74% parachlorotoluene; 0.07% dichlorotoluene; no detactable benzyl chloride; and a ratio of ortho:para isomers of 0.78.

EXAMPLE 9c

The procedure of Example 9a was repeated except that the reaction temperature was maintained at 50° C. Analysis of the resultant product indicated a composition of 40.95% toluene; 26.66% orthochlorotoluene; 32.29% parachlorotoluene; no detactable benzyl chloride; and a ratio of ortho:para isomers of 0.83.

EXAMPLE 10a

For purposes of comparison, the procedure of Example 9b was repeated except that in place of the co-catalyst employed therein there was substituted 0.60 parts of 2,3,7,8-tetramethylthianthrene. Analysis of the reaction product indicated a composition of 63.48% toluene; 20.55% orthochlorotoluene; 14.41% parachlorotoluene; 0.12% dichlorotoluene; and 1.44 benzyl chloride. The ratio of ortho:para isomers obtained was 1.43.

EXAMPLE 10b

For purposes of comparison, the procedure of Example 10a was repeated except that the reaction temperature was maintained at 50° C. Analysis of the reaction product indicated a composition of 39.52% toluene; 31.25% orthochlorotoluene; 27.60% parachlorotoluene; 0.19% dichlorotoluene; and 1.44 benzyl chloride. The ratio of ortho:para isomers obtained was 1.13.

From a comparison of Examples 10a and 10b with Examples 9a and 9b, respectively, it will be seen that although tetramethylthianthrene (Examples 10a and 10b) exhibits a weak para-directing effect, in the chlorination of toluene, a substantial improvement is achieved when a tetramethylthianthrene compound having electron-withdrawing substituents at the peri-positions is employed.

EXAMPLE 11

The procedure of Example 4 was repeated except that the reaction temperature was maintained at 60° C. Analysis of the reaction product indicated a composition of 62.1% toluene; 18.24% orthochlorotoluene; 20.51% parachlorotoluene; 0.106% dichlorotoluene; and no detectable benzyl chloride. The ratio of ortho:para isomers obtained was 0.89.

EXAMPLE 12

The procedure of Example 11 was repeated except that the quantity of Fe catalyst was doubled (0.025 parts). Analysis of the reaction product indicated a composition of 52.4% toluene; 22.08% orthochlorotoluene; 26.4% parachlorotoluene; 0.071% dichlorotoluene; and no detectable benzyl chloride. The ratio of ortho:para isomers obtained was 0.83.

EXAMPLE 13

For purposes of comparison, the procedure of Example 9a was repeated except that in place of the co-catalyst employed therein there was substituted 1,4,6,9-tetramethyl-2,3,7,8-tetrachlorothianthrene. Analysis of the reaction product indicated a composition of 63.18% toluene; 19.27% orthochlorotoluene; 17.19% parachlorotoluene; 0.17% dichlorotoluene; and 0.19% benzyl chloride. The ratio of ortho:para isomers obtained was 1.12.

From Example 13 it will be seen that when an electron donating substituent is present at each of the peri-positions of the thianthrene nucleus the para-directing effect in the chlorination of toluene is significantly weakened.

EXAMPLE 14

The procedure of Example 2 was repeated except that in place of the co-catalyst employed therein there was substituted the dimethylpentachlorothianthrene and dimethylhexachlorothianthrene mixture prepared in accordance with Example 1b. Analysis of the reaction product indicated a composition of 54.36% toluene; 19.53% orthochlorotoluene; 28.04% parachlorotoluene; 0.04% dichlorotoluene; and 0.03% benzyl chloride. The ratio of ortho:para isomers obtained was 0.70.

What is claimed is:

1. A process for the production of nuclear chlorinated alkylbenzenes comprises reacting, in the liquid phase, alkylbenzene with chlorine in the presence of a Lewis acid catalyst and a co-catalyst comprising a thianthrene compound or mixture of thianthrene compounds characterized by the formula:

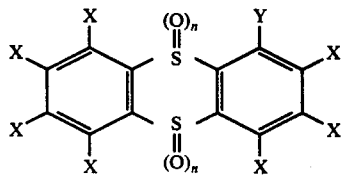

where $n$ is 0 to 1, y is an electron-withdrawing substituent or an electron-donating substituent and each x is hydrogen, an electron-withdrawing substituent or an electron-donating substituent; the total number of electron-withdrawing substituents present at the x and y positions is at least one and no more than seven; the total number of electron-donating substituents is at least one and no more than four; no more than three electron-donating substituents are present at the peri-positions; and with the proviso that when electron-withdrawing substituents are present at each of the peri-positions, electron-donating substituents are present at each of the 2, 3, 7 and 8 positions.

2. A process according to claim 1 wherein said electron-donating substituent is an alkyl or alkoxy substituent.

3. A process according to claim 2 wherein said electron-withdrawing substituent is selected from the group consisting of fluoro-, chloro-, bromo-, acetyl-, benzoyl-, and trifluoromethyl.

4. A process according to claim 3 wherein the alkylbenzene is toluene and the process is carried out at a temperature of about −30° to about 150° Celsius.

5. A process according to claim 4 wherein the Lewis acid catalyst is a halide, oxyhalide, oxide, sulfide, sulfate, carbonyl or elemental form of antimony, lead, iron, molybdenum, or aluminum.

6. A process according to claim 5 wherein the co-catalyst is a thianthrene compound or mixture of thianthrene compounds characterized by the formula shown wherein each $n$ is 0.

7. A process according to claim 6 wherein the electron-donating substituent is methyl.

8. A process according to claim 7 wherein the electron-withdrawing substituent is chloro-.

9. A process according to claim 8 wherein the co-catalyst is a thianthrene compound or mixture of thianthrene compounds characterized by the formula shown wherein two to four methyl groups and four to six chloro groups are present on the thianthrene nucleus.

10. A process according to claim 9 wherein the co-catalyst is dimethylhexachlorothianthrene.

11. A process according to claim 9 wherein the co-catalyst is dimethylpentachlorothianthrene.

12. A process according to claim 9 wherein the co-catalyst is dimethyltetrachlorothianthrene.

13. A process according to claim 9 wherein the co-catalyst is a mixture of dimethylhexachlorothianthrene, dimethylpentachlorothianthrene and dimethyltetrachlorothianthrene.

14. A process according to claim 9 wherein the co-catalyst is tetramethyltetrachlorothianthrene.

15. A process according to claim 9 wherein the Lewis acid catalyst is Fe.

16. A process according to claim 9 wherein the Lewis acid catalyst is an antimony halide.

17. A process according to claim 9 wherein the Lewis acid catalyst is antimony pentachloride.

18. A process according to claim 17 wherein the reaction temperature is about −20° to about 110° Celsius.

19. A process according to claim 18 wherein the catalyst system comprises about 0.01 to about 5.0 percent by weight based on the amount of toluene, and the molar ratio of catalyst:co-catalyst is about 0.01:1 to about 10:1.

20. A process according to claim 19 wherein the catalyst system comprises about 0.01 to about 2.0 percent by weight based on the amount of toluene, and the molar ratio of catalyst:co-catalyst is about 0.1:1 to about 1:1.

* * * * *